US00PP16836P2

(12) United States Plant Patent

Goffreda et al.

(10) Patent No.: US PP16,836 P2

(45) Date of Patent: Jul. 18, 2006

(54) PEACH TREE NAMED 'H28-52-96270'

(50) Latin Name: *Prunus persica*
Varietal Denomination: H28-52-96270

(75) Inventors: Joseph C. Goffreda, Millstone Township, NJ (US); Anna M. Voordeckers, East Windsor Township, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 66 days.

(21) Appl. No.: 11/039,196

(22) Filed: Jan. 18, 2005

(51) Int. Cl.
*A01H 5/00* (2006.01)

(52) U.S. Cl. ..... Plt./197

(58) Field of Classification Search ..... Plt./197
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct peach variety of *Prunus persica* named 'H28-52-96270' is provided. This variety is distinguished from other peach varieties by its unique combination of large showy pink flowers, red coloring of young foliage, flat fruit shape, and high quality nonmelting fruit that ripens in early midseason.

7 Drawing Sheets

Latin name of the genus and species of the plant claimed: *Prunus persica* L.
Variety denomination: 'H28-52-96270'.

BACKGROUND OF THE INVENTION

The present invention relates to a new and distinct variety of peach tree named 'H28-52-96270'. Our new tree resulted from crossing B7-6-151-752080 (unpatented) as the seed parent with NJF4 peach tree (unpatented), as the pollen parent. The resulting tree was selected when growing in a cultivated area as the 52$^{nd}$ tree in the 28$^{th}$ row of Block H at the Rutgers Fruit Research and Extension Center in Cream Ridge, N.J.

BRIEF SUMMARY OF THE INVENTION

The 'H28-52-96270' variety is distinguished from other peach varieties due to the following unique combination of characteristics: large showy pink flowers, red coloring of young foliage, flat fruit shape, and high quality nonmelting fruit that ripens in early midseason. For example, the new variety differs from seed parent 'B7-6-151-752080' (unpatented) in that the new variety has flat fruit while the parent has round fruit. The new variety differs from pollen parent 'NJF4' (unpatented) in that the new variety has greyed-purple leaves RHS 187a to RHS 187b while the parent has green leaves (upper surface RHS 147a, lower surface 147b). Asexual reproduction of this new variety by budding onto 'Lovell' (unpatented) rootstock shows that the foregoing characteristics come true to form, are firmly fixed, and are established and transmitted through succeeding propagations.

The following detailed description concerns the original tree, 'H28-52-96270' discovered on Aug. 4, 1999 and progeny first asexually propagated in August 2001 at the Rutgers Fruit Research and Extension Center in Cream Ridge, N.J. The original tree and progeny have been observed growing in a cultivated area at the Rutgers Fruit Research and Extension Center in Cream Ridge, N.J.

Certain characteristics of this variety, such as growth and color, may change with changing environmental conditions (such as, light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

Figure 1:
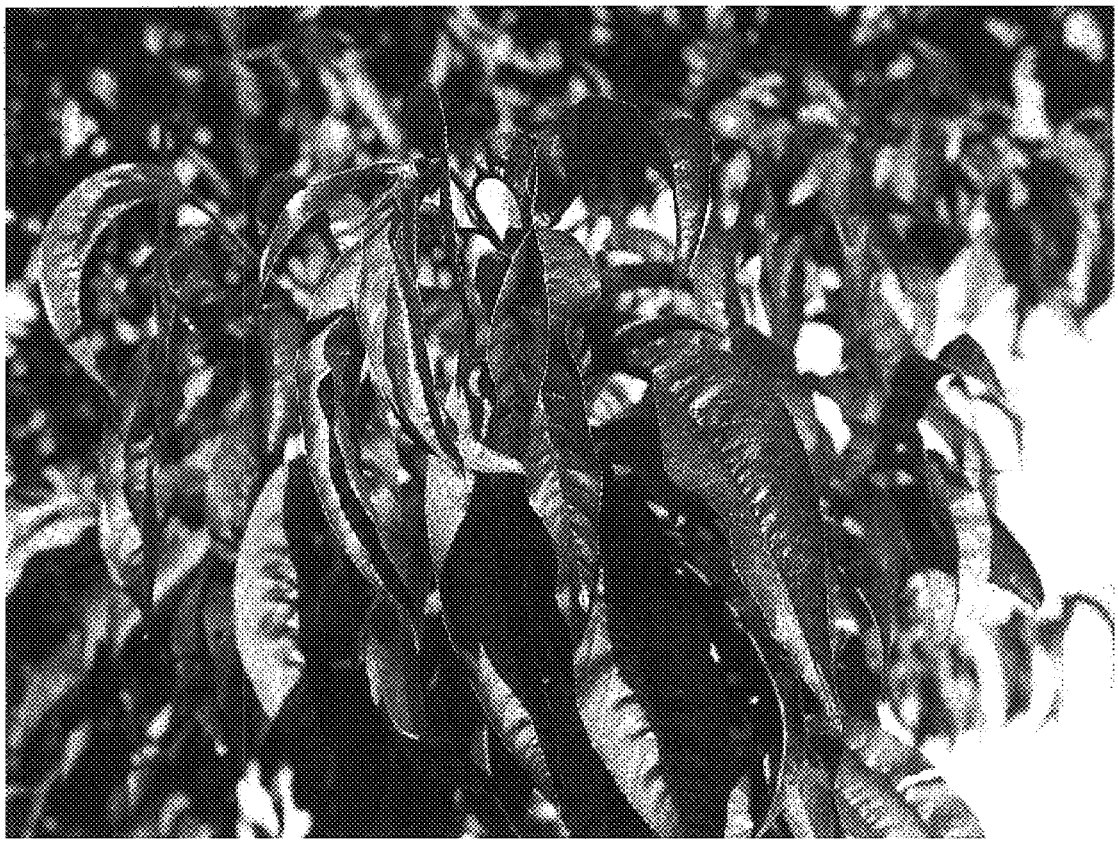
FIG. 1 is a color photograph of a characteristic twig of the new variety in early summer bearing typical leaves and illustrates the ornamental quality of the upper and lower leaf surface of the foliage.
Figure 2:
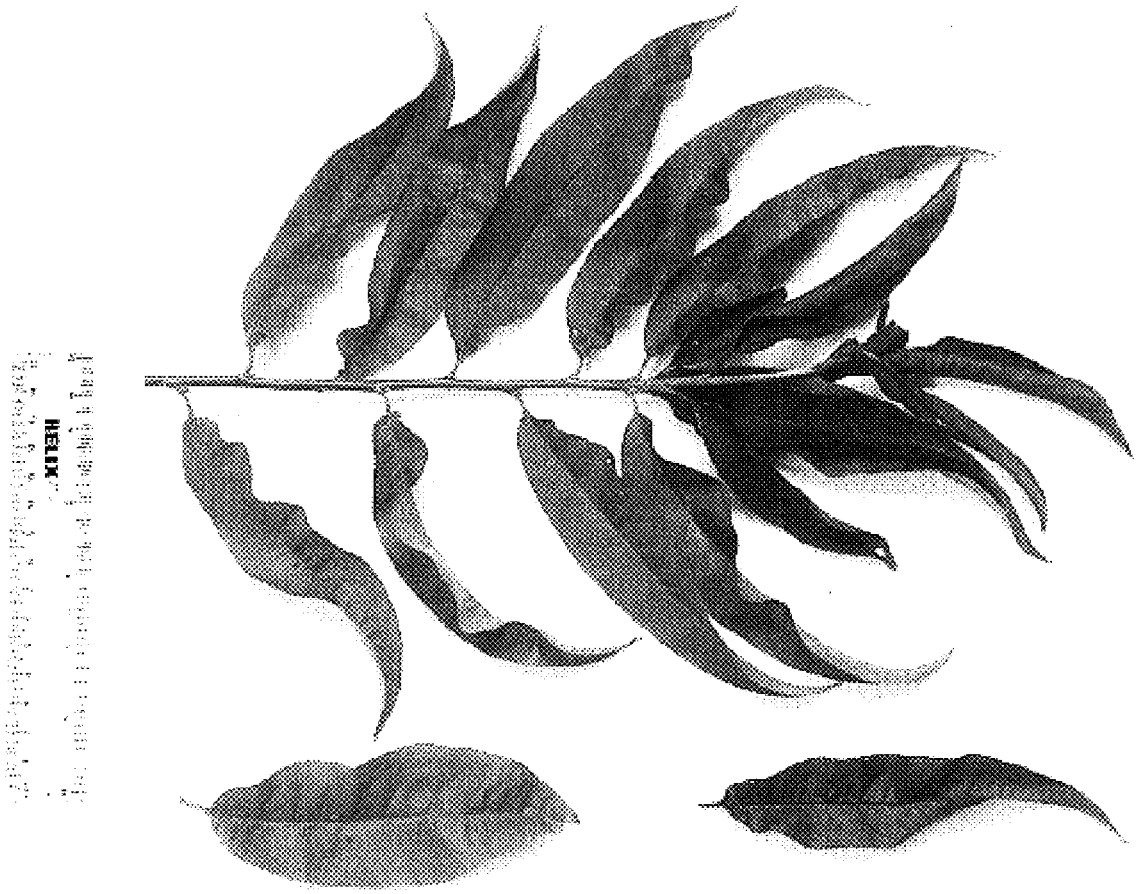
FIG. 2 is a color photograph of a characteristic twig of the new variety in late summer bearing typical leaves and illustrates the difference in color between young and mature foliage.
Figure 3:
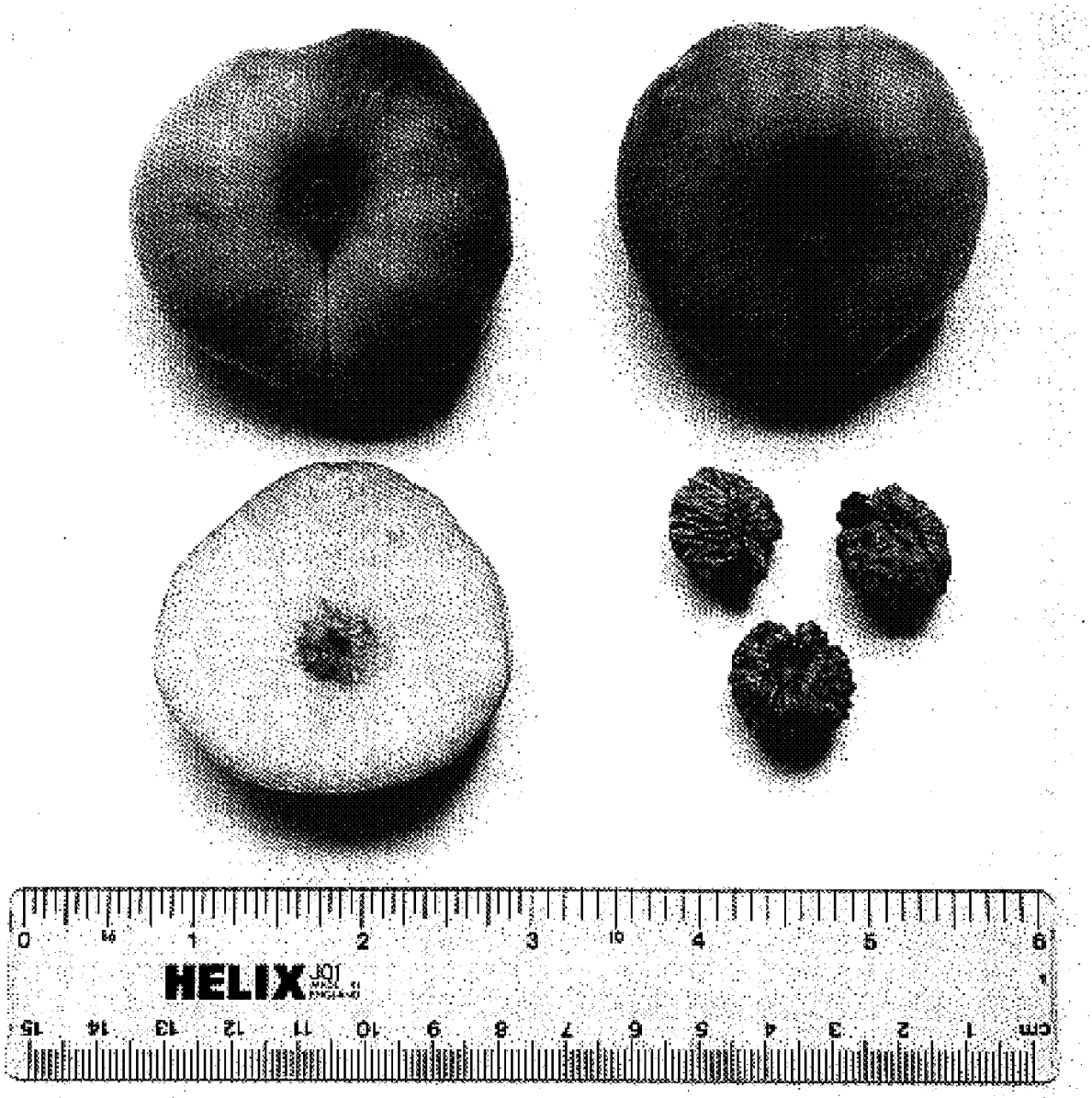
FIG. 3 is a color photograph of mature fruit of the new variety and stones harvested from the Rutgers Fruit Research and Extension Center in Cream Ridge, N.J. on Aug. 8, 2003. Whole fruit are presented in two positions and a cross section to show that the pericarp adheres to the pit when the fruit is mature. The stones illustrate the high, broad, and very deep dorsal ridge on the stone and the mixture of pits and chains of pits forming grooves on the surface of the stone.
Figure 4:
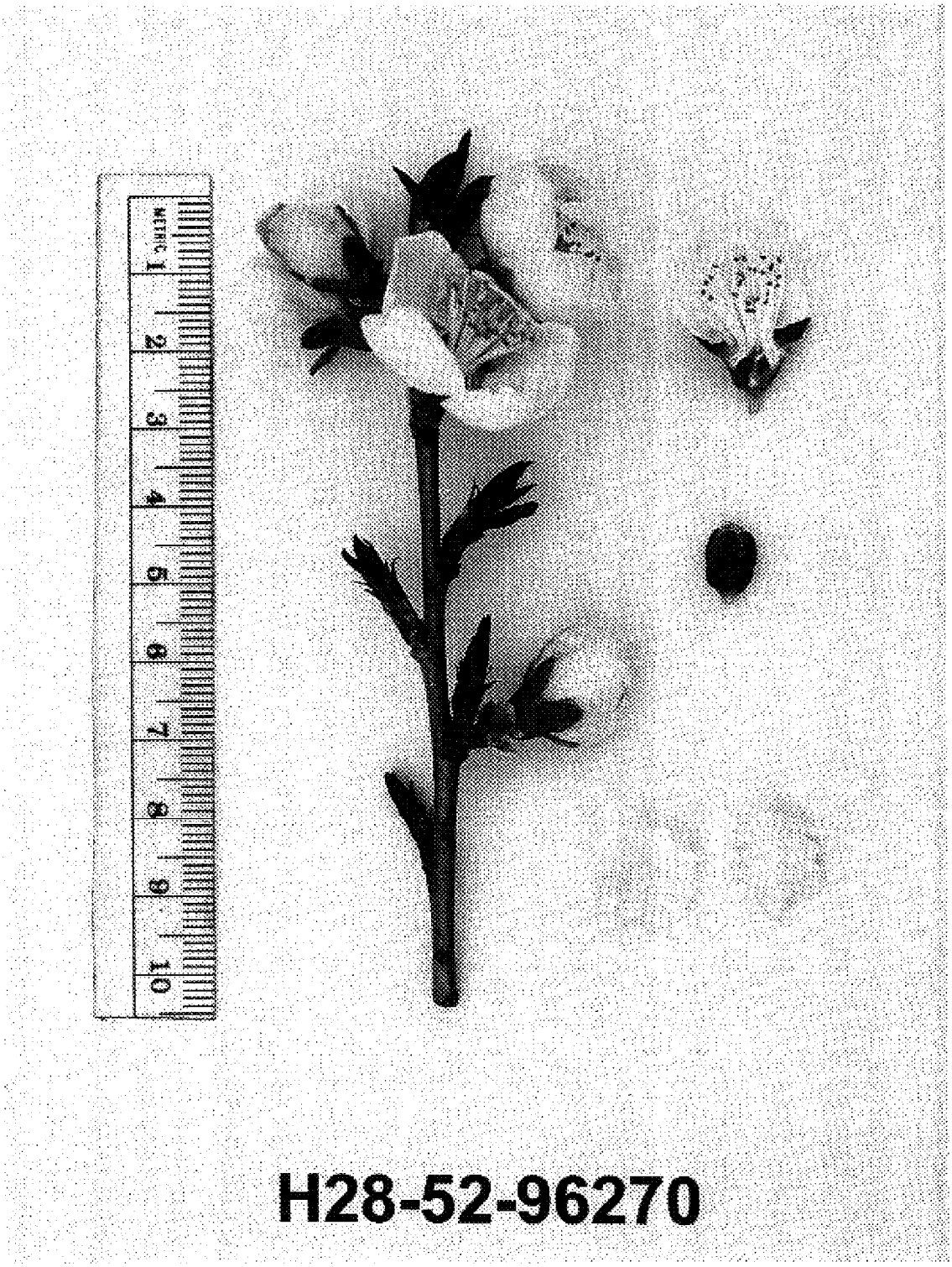
FIG. 4 is a color photograph of a characteristic twig that illustrates the typical flower buds and showy flowers of the new variety observed on a tree at the Rutgers Fruit Research and Extension Center in Cream Ridge, N.J.
Figure 5:
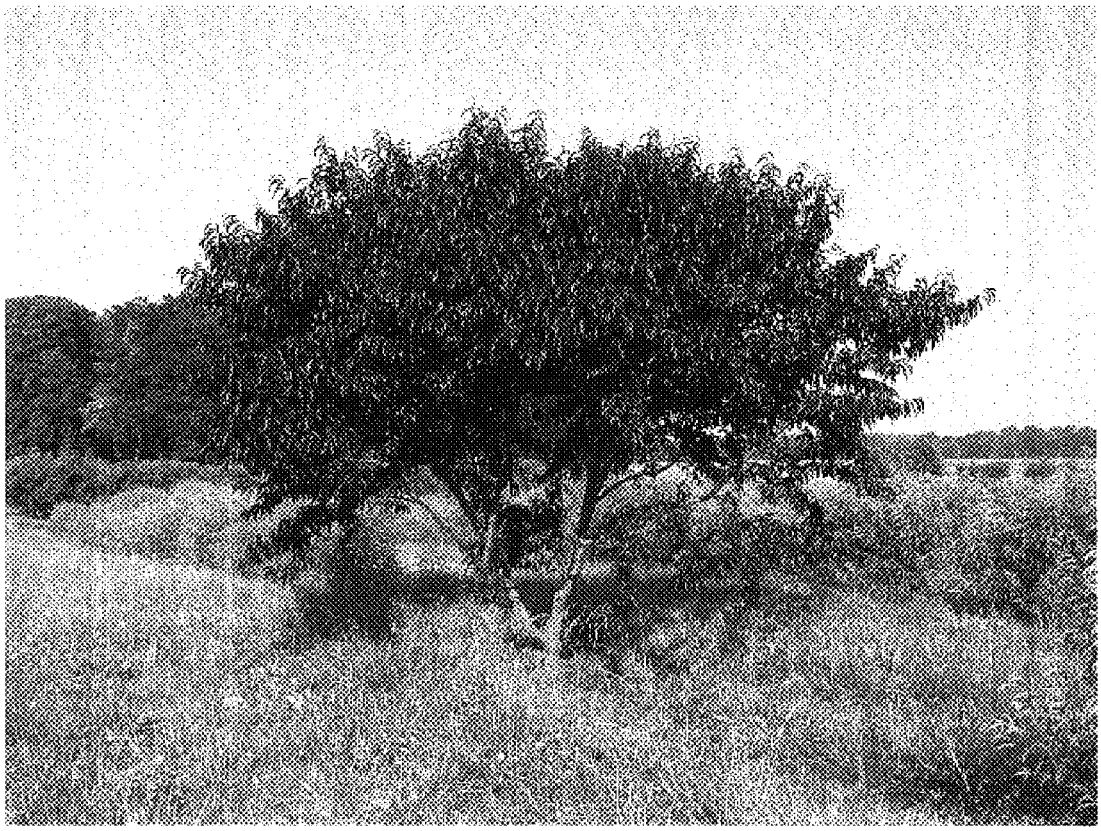
FIG. 5 is a color photograph of the new variety in early summer that illustrates the spreading growth habit and ornamental qualities of the foliage of a tree at the Rutgers Fruit Research and Extension Center in Cream Ridge, N.J.
Figure 6:
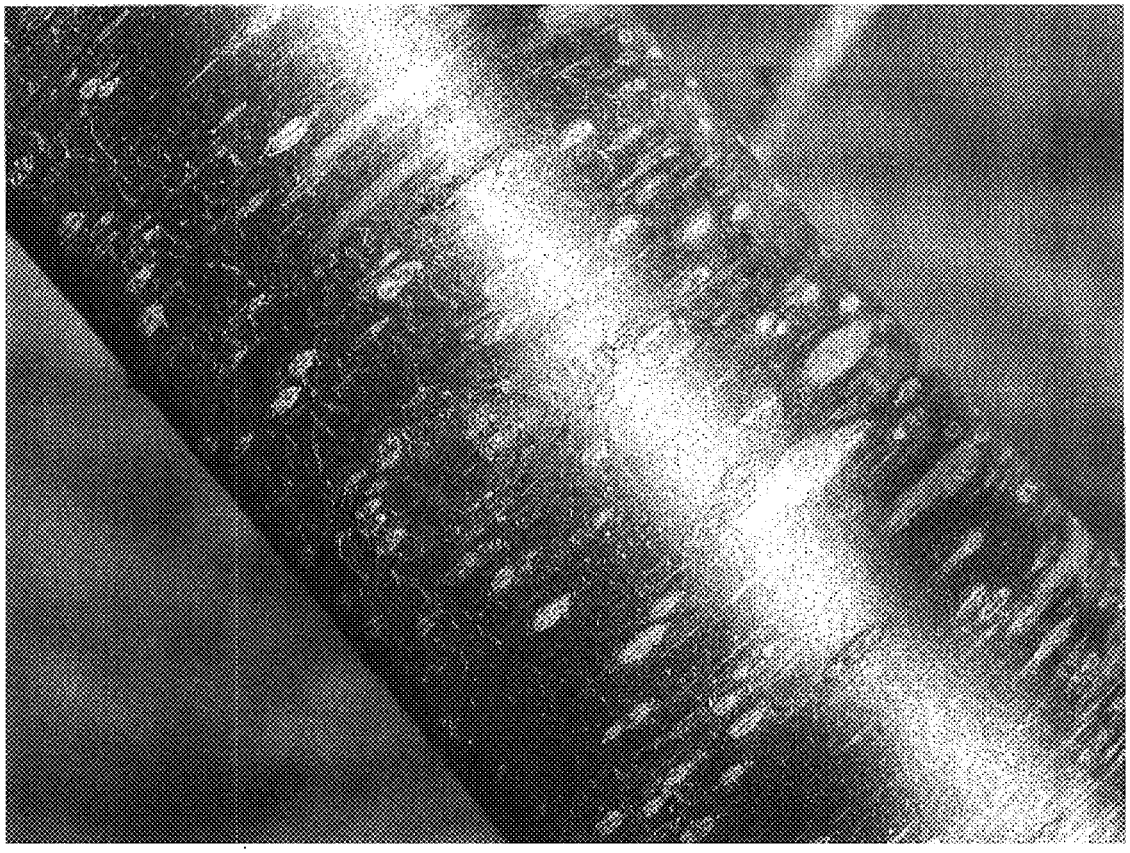
FIG. 6 is a color photograph of immature bark of the new variety that illustrates color and the moderate density of long lenticels on the immature bark.
Figure 7:
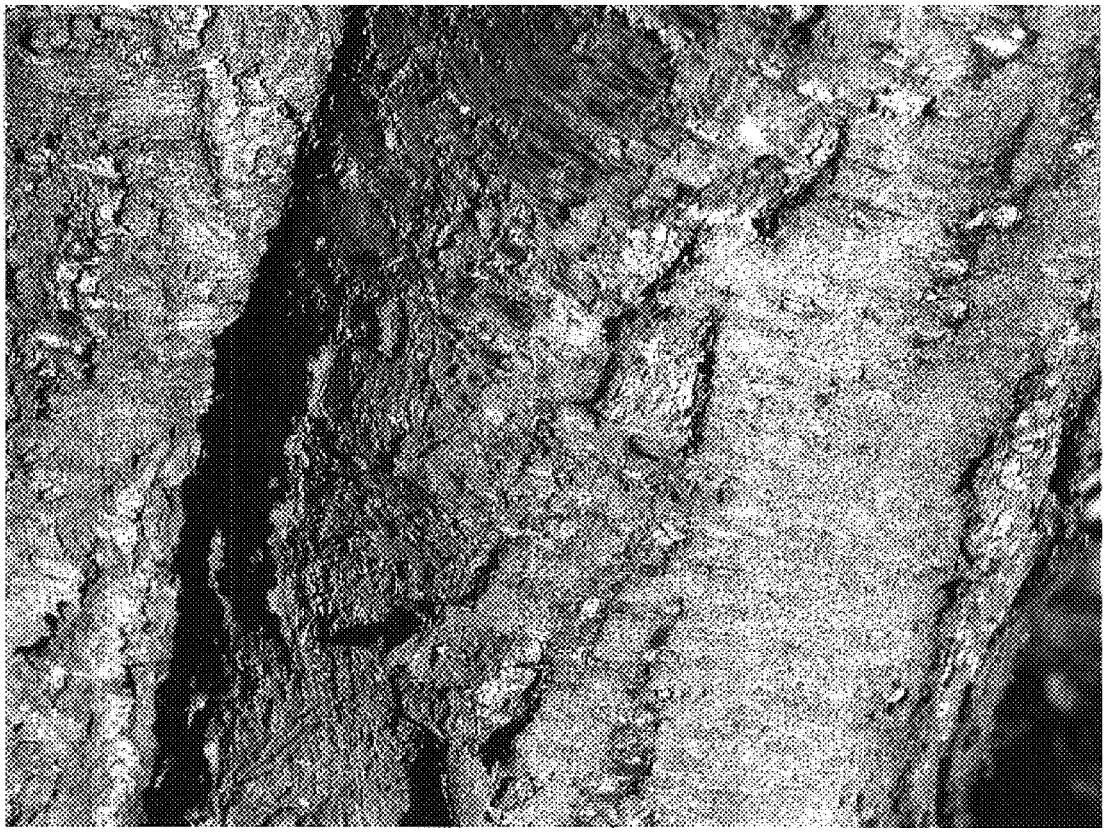
FIG. 7 is a color photograph of mature bark of the new variety that illustrates the moderately rough texture of the mature bark.

The color photographs show typical specimens of the leaves, flowers, fruit, and bark of this new peach tree variety and depict the color as nearly true as is reasonably possible to make the same in a color illustration of this character. It should be noted that colors may vary, for example due to lighting conditions at the time the photographs are taken. Therefore, color characteristics of this new variety should be determined with reference to the observations described herein, rather than from the photographs alone.

DETAILED BOTANICAL DESCRIPTION

The following detailed description of the 'H28-52-96270' variety is based on observations of the original seedling tree. The observed tree was 7 years of age and growing on its own roots in Research Block H at the Rutgers Fruit Research and Extension Center in Cream Ridge, N.J.

Scientific name: *Prunus persica* L.

Parentage:

*Seed parent.*—'B7-6-151-752080' (unpatented).

*Pollen parent.*—'NJF4' (unpatented).

Tree:

*Vigor.*—Vigorous.

*Overall shape.*—Spreading with a well rounded canopy.

*Height.*—Above average as compared to other peach cultivars. Measurement of original tree at 6 years after planting shows a height of 5 meters when grown in Cream Ridge, N.J.

*Width.*—Above average as compared to other peach cultivars. Measurement of original tree at 6 years after planting shows a width of 8 meters when grown in Cream Ridge, N.J.

*Caliper.*—Seven year old tree is 80 cm in circumference measured 15 cm from the ground.

*Trunk.*—Trunk bark texture: Moderately rough. Trunk bark color: Under color is greyed-red (RHS 178a) overlaid by grey (RHS 201b).

*Lenticels.*—Moderate density, approximately 8 per square inch; typical examples of which measured 5 mm in length; orange-white (RHS 159a) in color.

*Primary branches.*—Circumference 35 cm at 40 cm above the crotch. Color: One year old branches are greyed-red (RHS 178a) in color, while two year old branches are brown (RHS 200c) in color and overlaid with grey-green (RHS 198b). Branch pubescence: None. New growth bark: Greyed-red (RHS 178a) in color. Internodes: Average internode length is 2 cm on a one-year shoot.

Leaves: The length, width, thickness, and other measurements were obtained from observations of ten typical leaves in 2004.

*Texture.*—Glabrous.

*Sheen.*—Young leaves semi-glossy developing a satin finish when fully mature.

*Length.*—About 150 mm to 175 mm averaging about 160 mm including the petiole.

*Width.*—About 36 mm to 44 mm averaging about 40 mm.

*Petiole.*—About 10 mm long and about 1.5 mm in diameter.

*Margin.*—Serrulate.

*Margin undulation.*—Medium.

*Form.*—Lanceolate.

*Apex.*—Sharply acute, curved downward.

*Base.*—Broadly acute.

*Venation.*—Pinnate.

*Glands.*—Number: Two. Position: Located on petiole, adjacent to the leaf blade. Size: Small to medium with an average length of 1.5 mm and an average width of 0.7 mm when grown in Cream Ridge, N.J. Form: Reniform.

*Stipules.*—Not present on mature leaves. But are present on immature leaves (2 per leaf, limited to the growing tip. Average size is 7 mm).

*Leaf color.*—Upper leaf surface: Young leaves greyed-purple (RHS 187a to RHS 187b) and maturing to yellow-green (RHS 147a). Lower leaf surface: Young leaves greyed-purple (RHS 187a to RHS 187b) and maturing to yellow-green (RHS 148a to RHS 148b). Vein: Greyed-red (RHS 182a to 182b).

*Pubescence.*—None.

Flowers:

*Size.*—Large size, typical flower measuring about 36.9 mm across.

*Color.*—Dormant bud: Between grey (RHS 201b) and greyed-green (RHS 197c). Pink stage bud: Red-purple (between RHS 62c and RHS 62d). Open flower: Young open flowers red-purple (RHS 62d), darkening to red-purple (RHS 62c) at petal fall.

*Petals.*—Typically 5 petals per flower; nearly round shape; about 18.5 mm long (to slightly larger) and 15.7 (to slightly smaller) mm wide. Red-purple (between RHS 62d and RHS 62c) in color.

*Petal apex.*—Acute.

*Petal base.*—Obtuse.

*Stamens.*—Typically 40 stamens and green-white (RHS 157c) in color.

*Pistil.*—About 15.2 mm long and greyed-yellow (between RHS 160b and RHS 160c) in color.

*Sepals.*—Greyed-red (RHS 182b) in color, with light pubescence.

*Pollen.*—Abundant; yellow (RHS 11a) in color.

*Fragrance.*—Slight.

*Bloom season.*—In 2004 in Cream Ridge, N.J., onset of bloom on April 17; full bloom on April 19; petal fall on April 22. Flower cold tolerance has been observed to −16° C. in Cream Ridge, N.J.

*Stamens.*—Average length of 12 mm.

*Pistils.*—Average one in number.

*Sepals.*—Five in number. Shape triangular, with a rounded apex. Color varies between RHS 62b to 62d. Average length of 5.6 mm and an average width of 4.0 mm.

Fruit: (Observations from a limited number of typical fruit grown in Cream Ridge, N.J.).

*Size.*—Medium, about 3.2 cm long, 5.5 cm wide perpendicular to the suture and 5.3 cm wide parallel to the suture.

*Typical weight.*—55.9 g.

*Form.*—Longitudinal section: Oblate. Traverse section: Nearly round.

*Suture.*—Very shallow.

*Ventral surface.*—Rounded.

*Base.*—Truncated and indented.

*Apex.*—Depressed; between 1 mm to 7 mm in diameter, with an average of 4.4 mm.

*Skin.*—Thickness: Average. Surface: Regular with short pubescence. Tenacity: Above average. Astringency:

None. Tendency to crack: Very low. Color: Over color red (RHS 47a); mottling between orange (RHS 26a) and orange (RHS 26b); under color orange (RHS 24b).

*Fruit properties.*—Flesh color: Between yellow-orange (RHS 21b) and yellow-orange (RHS 21c). Flesh adhesion: Clingstone. Juice: Moderate. Texture: Fine, nonmelting. Fibers: Not noticeable. Ripens: Between July 23 and August 5 at Cream Ridge, N.J. Flavor: Spicy. Soluble solids: 12.5%. Aroma: Strong. Eating quality: High.

*Fruit stem.*—Average length of 6.5 mm and an average diameter of 7.8 mm.

*Fruit production.*—In 2003, first picking date in Cream Ridge, N.J. was about July 30 and last picking was about August 5.

*Usage.*—Fresh market.

*Fruit productivity.*—Very good for a flat peach. Original tree has produced a crop in 5 out of 6 years, and a full crop in 3 out of 6 years.

*Keeping quality.*—Good. Held its flavor and firmness for at least 14 days in cold storage at 1° to 4° C.

*Shipping quality.*—Good. No specific bruising or scaring disorders have been observed.

Stone:

*Type.*—Clingstone.

*Form.*—Oblate.

*Base.*—Very broad.

*Apex.*—Very broad.

*Surface.*—Mixture of pits and chains of pits forming grooves.

*Dorsal ridge.*—High, broad, and very deep.

*External color.*—Between greyed-orange (RHS 165b) and greyed-orange (RHS 165c).

*Internal color when cracked.*—Greyed-orange (RHS 165d).

*Cavity surface color.*—Greyed-orange (RHS 165c).

*Average stone wall thickness.*—4.3 mm.

*Average width.*—18.9 mm.

*Average length.*—17.5 mm.

*Average breadth.*—13.1 mm.

*Tendency to split.*—None.

*Kernel.*—Form: Irregular. Skin color: Greyed-orange (RHS 165b). Vein color: Greyed-orange (RHS 164a). Viable: No. Size: Highly variable; forms only rudimentary seed. Weight: Average dry weight of 1.7 g.

Plant/fruit disease and pest resistance/susceptibility: None observed.

Plant hardiness zone: Growth of plants has only been observed in zone 6b.

We claim:

1. A new and distinct variety of peach tree, substantially as herein shown and described.

* * * * *